(12) United States Patent
Kassab et al.

(10) Patent No.: US 9,517,148 B2
(45) Date of Patent: Dec. 13, 2016

(54) DEVICES, SYSTEMS, AND METHODS FOR THE PREVENTION OF STROKE

(75) Inventors: Ghassan S. Kassab, Zionsville, IN (US); Jose A. Navia, Sr., Buenos Aires (AR); Jorge Jordana, Buenos Aires (AR)

(73) Assignee: CVDevices, LLC, San Diego, CA (US)

( * ) Notice: Subject to any disclaimer, the term of this patent is extended or adjusted under 35 U.S.C. 154(b) by 202 days.

(21) Appl. No.: 13/264,508

(22) PCT Filed: Apr. 16, 2010

(86) PCT No.: PCT/US2010/031475
§ 371 (c)(1),
(2), (4) Date: Oct. 14, 2011

(87) PCT Pub. No.: WO2010/121192
PCT Pub. Date: Oct. 21, 2010

(65) Prior Publication Data
US 2012/0041471 A1 Feb. 16, 2012

Related U.S. Application Data

(60) Provisional application No. 61/169,767, filed on Apr. 16, 2009.

(51) Int. Cl.
*A61M 29/00* (2006.01)
*A61F 2/90* (2013.01)
(Continued)

(52) U.S. Cl.
CPC . *A61F 2/90* (2013.01); *A61F 2/95* (2013.01); *A61F 2/966* (2013.01);
(Continued)

(58) Field of Classification Search
CPC ............... A61F 2/01; A61F 2/82; A61F 2/86; A61F 2/90; A61F 2/966; A61F 2002/821; A61F 2230/0067; A61F 2250/0039
(Continued)

(56) References Cited

U.S. PATENT DOCUMENTS 5,332,402 A    7/1994  Teitelbaum
5,868,777 A *  2/1999  Lam .......................... A61F 2/90
                                              606/194

(Continued)

FOREIGN PATENT DOCUMENTS

JP         1221155       9/1989

OTHER PUBLICATIONS

Internationel Searching Authority, International Search Report, dated Jun. 15, 2010.
(Continued)

*Primary Examiner* — Robert Lynch
(74) *Attorney, Agent, or Firm* — Reichel Stohry LLP; Mark C. Reichel; Natalie J. Dean

(57) ABSTRACT

The disclosure of the present application provides devices, systems, and methods for the prevention of stroke. In at least one embodiment of a device of the present application, the device comprises an extension portion sized and shaped to fit within an artery extending from an aortic arch, and a flange portion sized and shaped to prevent the device from advancing into the artery extending from the aortic arch in which the device may be positioned. In at least one embodiment of a system for preventing stroke of the present application, the system comprises a hypotube, a folder coupled to a distal end of the hypotube, a sleeve positioned circumferentially around the hypotube proximal to the folder, and a stent, wherein a first part of the stent may be
(Continued)

positioned within the folder, and wherein a second part of the stent may be positioned within the sleeve.

26 Claims, 9 Drawing Sheets

(51) Int. Cl.
*A61F 2/95* (2013.01)
*A61F 2/966* (2013.01)
*A61F 2/82* (2013.01)

(52) U.S. Cl.
CPC . *A61F 2002/821* (2013.01); *A61F 2230/0067* (2013.01); *A61F 2250/0039* (2013.01)

(58) Field of Classification Search
USPC ....... 606/191, 198, 200; 623/1.1, 1.11, 1.12, 623/1.13, 1.15, 1.24, 1.26, 1.31, 1.35, 1.36, 623/1.39, 2.1, 2.17, 2.18, 2.38, 900, 902; 128/897, 898
See application file for complete search history.

(56) References Cited

U.S. PATENT DOCUMENTS

| | | | |
|---|---|---|---|
| 5,935,139 A | 8/1999 | Bates | |
| 5,944,738 A | 8/1999 | Amplatz et al. | |
| 6,096,071 A * | 8/2000 | Yadav | 623/1.15 |
| 6,309,399 B1 | 10/2001 | Barbut et al. | |
| 6,361,545 B1 | 3/2002 | Macoviak et al. | |
| 6,419,686 B1 * | 7/2002 | McLeod | A61B 17/12022 606/200 |
| 6,499,487 B1 | 12/2002 | McKenzie et al. | |
| 6,508,833 B2 * | 1/2003 | Pavcnik | A61F 2/07 623/1.15 |
| 6,682,543 B2 | 1/2004 | Barbut et al. | |
| 6,695,858 B1 | 2/2004 | Dubrul et al. | |
| 6,740,112 B2 | 5/2004 | Yodfat et al. | |
| 7,244,267 B2 | 7/2007 | Huter et al. | |
| 7,367,985 B2 | 5/2008 | Mazzocchi et al. | |
| 7,455,688 B2 * | 11/2008 | Furst | A61F 2/82 623/1.31 |
| 7,479,153 B2 | 1/2009 | Belef | |
| 7,493,162 B2 | 2/2009 | Girouard et al. | |
| 7,537,600 B2 | 5/2009 | Eskuri | |
| 2003/0158574 A1 | 8/2003 | Esch et al. | |
| 2004/0064092 A1 | 4/2004 | Tsugita et al. | |
| 2005/0159773 A1 | 7/2005 | Broome et al. | |
| 2005/0267516 A1 * | 12/2005 | Soleimani et al. | 606/200 |
| 2006/0015138 A1 | 1/2006 | Gertner | |
| 2007/0179592 A1 | 8/2007 | Schaeffer | |
| 2007/0208410 A1 | 9/2007 | Berra et al. | |
| 2008/0140110 A1 | 6/2008 | Spence | |
| 2008/0255603 A1 * | 10/2008 | Naor et al. | 606/200 |
| 2009/0099647 A1 | 4/2009 | Glimsdale et al. | |
| 2009/0254172 A1 * | 10/2009 | Grewe | 623/1.15 |
| 2013/0218194 A1 * | 8/2013 | Jonsson | A61F 2/01 606/200 |

OTHER PUBLICATIONS

Internationel Searching Authority (ISA), Written Opinion of ISA, dated Jun. 15, 2010.

* cited by examiner

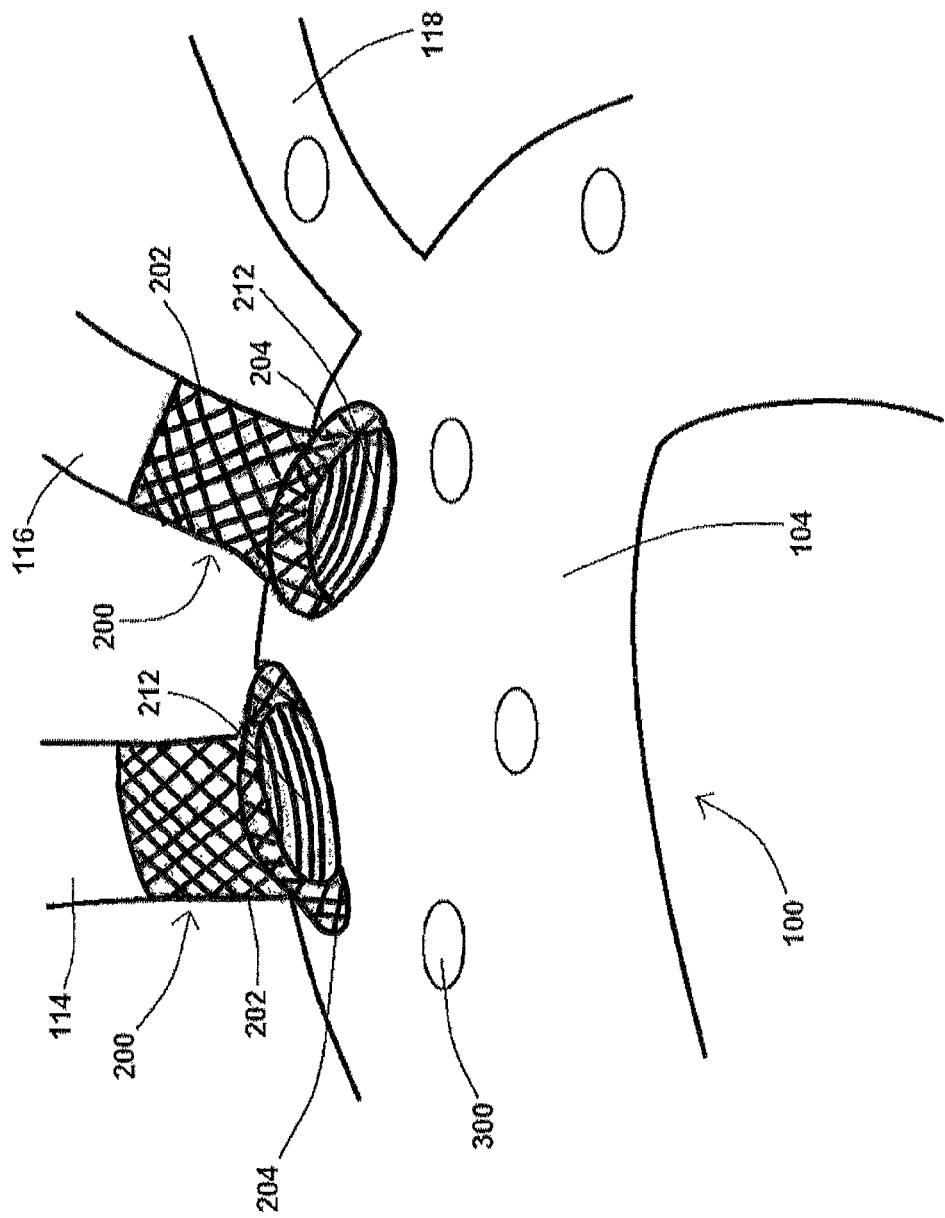

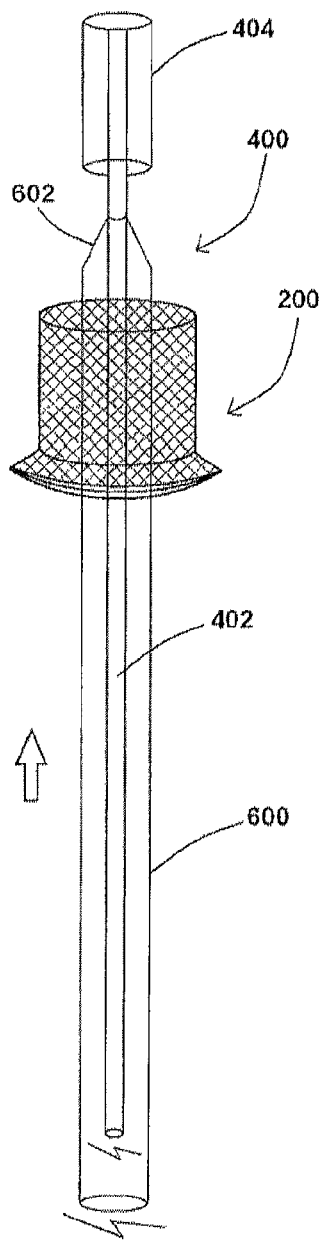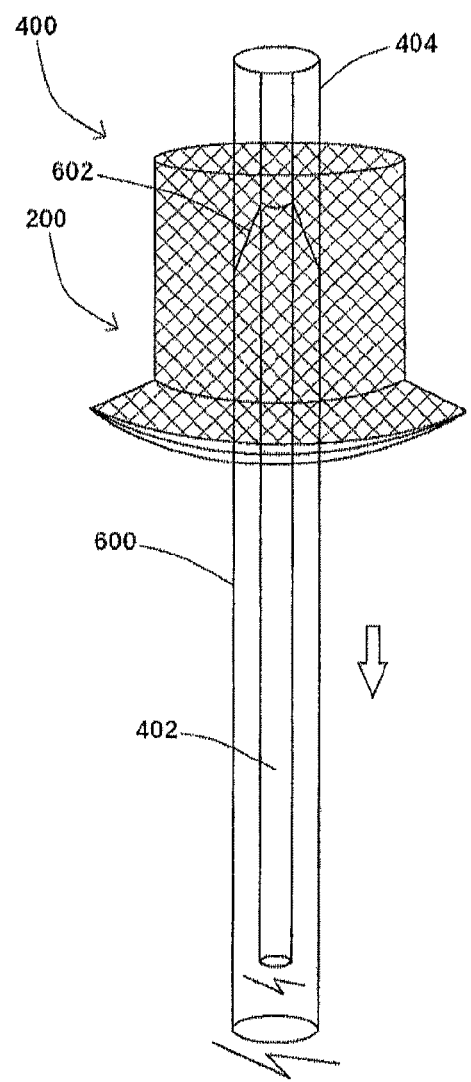
Fig. 7A
Fig. 7B

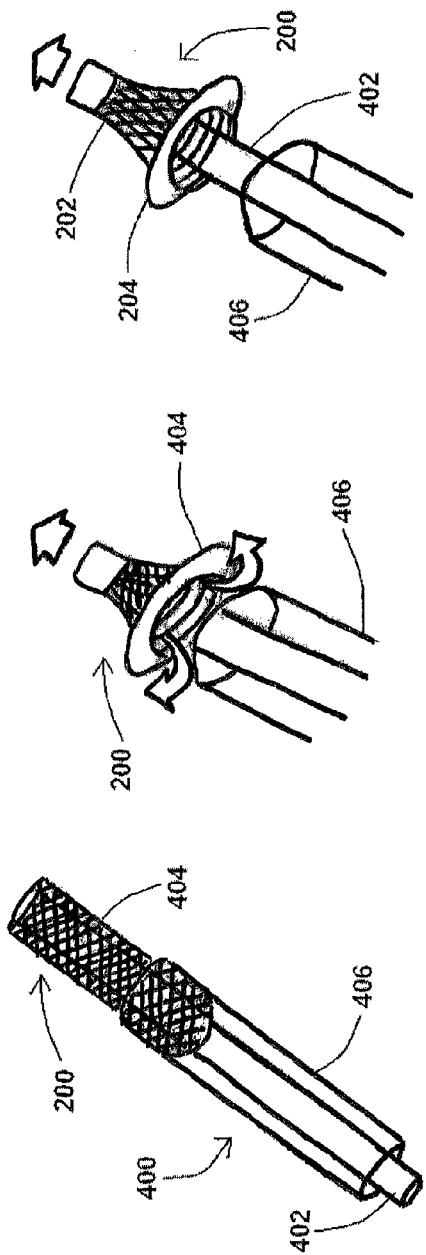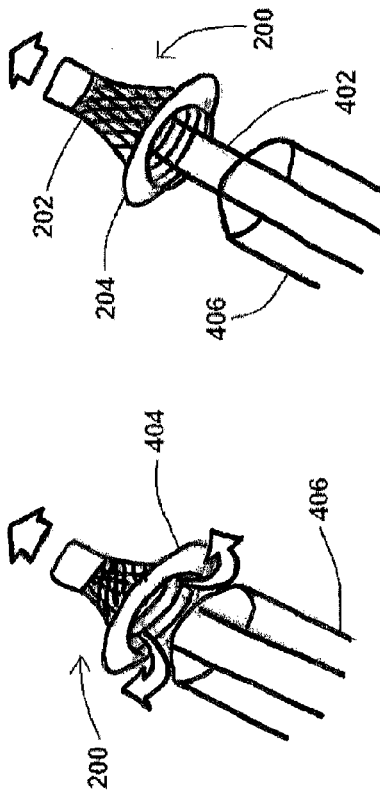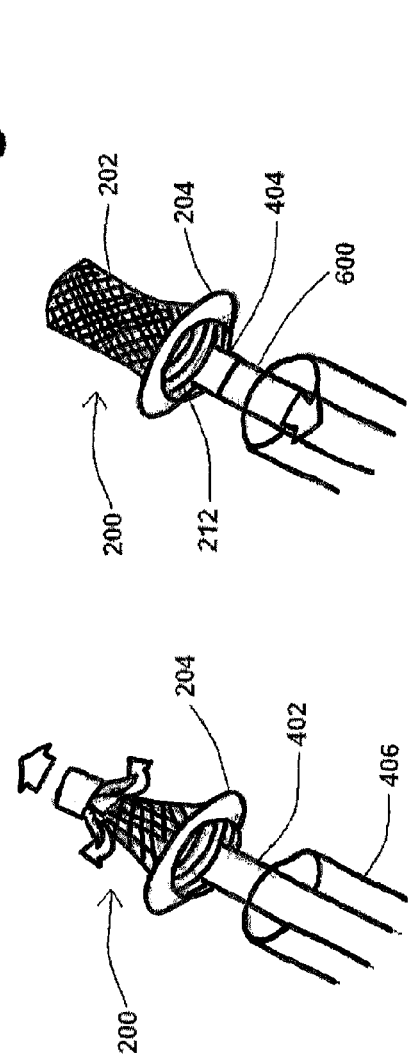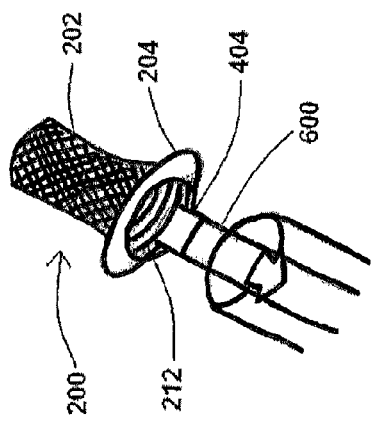

DEVICES, SYSTEMS, AND METHODS FOR THE PREVENTION OF STROKE

PRIORITY

The present application is related to, claims the priority benefit of and is a U.S. §371 national stage entry of, International Patent Application Ser. No. PCT/US2010/031475, filed Apr. 16, 2010, which is related to, and claims the priority benefit of, U.S. Provisional Patent Application Ser. No. 61/169,767, filed Apr. 16, 2009. The contents of each of these applications are hereby incorporated by reference in their entirety into this disclosure.

BACKGROUND

Stroke

A stroke is defined as a rapidly developing loss of brain function due to a disturbance in the blood supply to the brain. This can be due to ischemia (lack of blood supply) caused by thrombosis or embolism or due to a hemorrhage. As a result, the affected area of the brain is unable to function, leading to the inability to move one or more limbs on one side of the body, the inability to understand or formulate speech, or the inability to see one side of the visual field amongst others.

Each year, about 800,000 people experience a new or recurrent stroke. Approximately 600,000 of these are first attacks, and 200,000 are recurrent attacks. In addition, and on average, someone in the U.S. has a stroke every 40 seconds, and each year, about 55,000 more women than men have a stroke. On average, every 3-4 minutes, someone dies of a stroke. Because women live longer than men, more women than men die of stroke each year. Women accounted for 60.6% of U.S. stroke deaths in 2005. Men stroke incidence rates are greater than women at younger ages but not at older ages. Despite advances in stroke prevention treatments, the incidence of hospitalized stroke and case fatality did not decrease. African-Americans have almost twice the risk of first-ever stroke than whites. The age adjusted stroke incidence rates in people 45-84 years of age are 6.6 per 1000 population in black men, 3.6 in white men, 4.9 in black women, and 2.3 in white women.

Of all strokes, 87% are ischemic, 10% are intracerebral hemorrhage, and 3% are subarachnoid hemorrhage strokes. Stroke accounted for about 1 out of every 17 deaths in the U.S. in 2005, and approximately 53% of stroke deaths in 2005 occurred out of the hospital.

Total stroke mortality in 2005 was about 150,000. The 2005 overall death rate for stroke was 46.6 per 100,000. Death rates were 44.7 for white males, 70.5 for black males, 44.0 for white females, and 60.7 for black females, all per 100,000. When considered separately from other cardiovascular diseases, stroke ranks no. 3 among all causes of death, behind heart disease and cancer.

A report released by the Centers for Disease Control (CDC) in collaboration with the Centers for Medicare and Medicaid Services (CMS), the *Atlas of Stroke Hospitalizations Among Medicare Beneficiaries*, found that in Medicare beneficiaries, 30-day mortality rate varied by age: 9% in patients 65 to 74 years of age, 13.1% in those 74 to 84 years of age, and 23% in those ≥85 years of age.

Atrial Fibrillation

Atrial fibrillation (AF) is an significant, independent risk factor for ischemic stroke, increasing risk about 5-fold. The percentage of strokes attributable to AF increases steeply from 1.5% at 50 to 59 years of age to 23.5% at 80 to 89 years of age. Most strokes in patients with AF are cardioembolic caused by embolism of left atrial appendage thrombi, but some are caused by coexisting intrinsic cerebrovascular diseases in typically elderly, often hypertensive patients.

AF carries an annual risk of thromboembolic complications of 3-6%, which is 5-7 times greater than that of controls with sinus rhythm. AF is present in 15-21% of patients affected by stroke. AF/flutter, a strong risk factor for stroke, is arguably the most important finding on cardiac workup in patients with ischemic stroke. Once identified, introduction of oral anticoagulant therapy (warfarin, for example) provides a 40% risk reduction in recurrent stroke compared with antiplatelet therapy. Ischemic stroke with AF is associated with greater disability and mortality than those without AF.

Patients with AF have an increased risk of major, disabling stroke, often caused by large infarctions in the middle cerebral artery territory. Some studies showed that AF was associated with an increased risk of death in the first four weeks after stroke likely due to the advanced age in stroke patients with AF, large infarction, severe neurological deficits, and poor functional outcomes.

First, strokes in patients with AF may largely be cardioembolic, which causes a sudden occlusion of large cerebral arteries without sufficient collateral blood flow, resulting in more severe strokes. Several studies have reported that stroke patients with AF often have large cortical infarcts on computed tomography, and less frequently have lacunar infarction as compared with patients without AF.

Heart Failure

Patients with heart failure (HF) are at increased risk for thromboembolic events. Left ventricular (LV) thrombus provides a substrate for events and a rationale for anticoagulation. Echocardiography studies have yielded conflicting results, however, regarding thrombus prevalence. Among populations with similar degrees of systolic dysfunction, studies have reported over a 20-fold difference in prevalence, ranging from 2.1% to 50%. Moreover, when thrombus is identified, conflicting findings have been reported concerning the risk of future embolic events.

The impact of nonrheumatic atrial fibrillation, hypertension, coronary heart disease, and cardiac failure on stroke incidence was examined in the Framingham Study. Compared with subjects free of these conditions, the age-adjusted incidence of stroke was more than doubled in the presence of coronary heart disease and more than tripled in the presence of hypertension. There was a more than fourfold excess of stroke in subjects with HF and nearly fivefold increase when atrial fibrillation was present. In persons with coronary heart disease or HF, atrial fibrillation doubled the stroke risk in men and tripled the risk in women. Factors that predispose to thromboembolic events in patients with HF include low cardiac output, with relative stasis of blood in dilated cardiac chambers, poor contractility and regional wall motion abnormalities and concomitant atrial fibrillation.

BRIEF SUMMARY

In at least one exemplary embodiment of a device for the prevention of stroke of the present disclosure, the device comprises an extension portion sized and shaped to fit within an artery extending from an aortic arch, and a flange portion sized and shaped to prevent the device from advancing into the artery extending from the aortic arch in which the device may be positioned, the flange portion comprising two or more parallel convex struts positioned across an opening defined within the flange portion, the two or more parallel convex struts capable of diverting an embolus from entering the artery when the device is positioned within the artery. In another embodiment, the two or more parallel convex struts comprises four or more parallel convex struts. In an exemplary embodiment, when the device is positioned within the artery extending from an aortic arch, the two or more parallel convex struts are positioned either approximately perpendicular to, or in a direction of, blood flow within the aortic arch. In an additional embodiment, the device comprises a stent. In yet an additional embodiment, the stent is autoexpandable.

In at least one exemplary embodiment of a device for the prevention of stroke of the present disclosure, the extension portion comprises a substantially cylindrical shape. In another embodiment, the extension portion comprises an extension mesh comprising multiple wires. In yet another embodiment, the extension portion has a length between about 1.5 cm to about 2.5 cm. In an additional embodiment, the extension portion has a diameter between about 6 mm to about 8 mm when the extension portion is in an expanded configuration. In yet an additional embodiment, the extension portion has a diameter between about 1.8 mm to about 2.0 mm when the extension portion is in a compressed configuration.

In at least one exemplary embodiment of a device for the prevention of stroke of the present disclosure, the device is comprised of a material selected from the group consisting of stainless steel, cobalt-chromium-nickel-molybdenum-iron alloy, tantalum, nitinol, nickel-titanium, polymer materials, and a shape-memory polymer. In an additional embodiment, the flange portion comprises a flange mesh comprising multiple wires. In another embodiment, the flange portion comprises a planar flange.

In at least one exemplary embodiment of a device for the prevention of stroke of the present disclosure, the device further comprises one or more radiopaque markers positioned upon the flange portion. In an additional embodiment, the one or more radiopaque markers are positioned relative to the two or more parallel convex struts. In yet additional embodiments, when the device positioned within the artery extending from an aortic arch, the one or more radiopaque markers facilitate alignment of the device so that the two or more parallel convex struts are positioned either approximately perpendicular to, or in a direction of, blood flow within the aortic arch.

In at least one exemplary embodiment of a device for the prevention of stroke of the present disclosure, the diameter of each of the two or more parallel convex struts is between about 0.25 mm and 0.5 mm. In another embodiment, the two or more parallel convex struts are positioned between about 0.5 mm to 1.5 mm from one another. In yet another embodiment, the two or more parallel convex struts are flexible.

In at least one exemplary embodiment of a device for the prevention of stroke of the present disclosure, the device comprises an extension portion sized and shaped to fit within an artery extending from an aortic arch, and a flange portion sized and shaped to prevent the device from advancing into the artery extending from the aortic arch in which the device may be positioned, the flange portion capable of diverting an embolus from entering the artery extending from the aortic arch when the device is positioned within the artery. In an additional embodiment, the device further comprises one or more radiopaque markers positioned upon the flange portion. In yet an additional embodiment, the device further comprises two or more convex parallel struts positioned across an opening defined with the flange portion, wherein the one or more radiopaque markers are positioned relative to the two or more parallel convex struts. In another embodiment, when the device positioned within the artery extending from an aortic arch, the one or more radiopaque markers facilitate alignment of the device so that the two or more parallel convex struts are positioned either approximately perpendicular to, or in a direction of, blood flow within the aortic arch.

In at least one exemplary embodiment of a device for the prevention of stroke of the present disclosure, the device further comprises two or more parallel convex struts positioned across an opening defined with the flange portion.

In at least one exemplary embodiment of a device for the prevention of stroke of the present disclosure, the device comprises an extension portion comprising a substantially cylindrical shape, the extension portion sized and shaped to fit within an artery extending from an aortic arch, a flange portion sized and shaped to prevent the device from advancing into the artery extending from the aortic arch in which the device may be positioned, the flange portion comprising two or more parallel convex struts positioned across an opening defined within the flange portion, the two or more parallel convex struts capable of diverting an embolus from entering the artery when the device is positioned within the artery, and one or more radiopaque markers positioned upon the flange portion, wherein when the device positioned within the artery extending from an aortic arch, the one or more radiopaque markers facilitate alignment of the device so that the two or more parallel convex struts are positioned either approximately perpendicular to, or in a direction of, blood flow within the aortic arch.

In at least one exemplary embodiment of a system for preventing stroke of the present disclosure, the system comprises a device for the prevention of stroke, the device comprising an extension portion sized and shaped to fit within an artery extending from an aortic arch, and a flange portion sized and shaped to prevent the device from advancing into the artery extending from the aortic arch in which the device may be positioned, the flange portion comprising two or more parallel convex struts positioned across an opening defined within the flange portion, the two or more parallel convex struts capable of diverting an embolus from entering the artery when the device is positioned within the artery, a hypotube having a distal end and a proximal end, a folder coupled to the distal end of the hypotube, the folder sized and shaped to receive at least a portion of the device for the prevention of stroke, and a sleeve positioned circumferentially around the hypotube proximal to the folder, the sleeve sized and shaped to receive at least a portion of the device for the prevention of stroke. In another embodiment, the system further comprises a conical dilator, the conical dilator sized and shaped to slidingly engage the hypotube. In yet another embodiment, the conical dilator comprises a tapered distal and a proximal end. In an additional embodiment, the folder has an inner diameter, and wherein the tapered distal end of the conical dilator is sized and shaped to fit within the inner diameter of the folder. In yet an additional embodiment, when the device is positioned within the artery extending from an aortic arch, the two or more parallel convex struts either approximately perpendicular to, or in a direction of, blood flow within the aortic arch.

In at least one exemplary embodiment of a system for preventing stroke of the present disclosure, the device of the system comprises a stent. In another embodiment the stent is autoexpandable. In yet another embodiment, the hypotube has an aperture defined therethrough from the distal end to the proximal end of the hypotube, said aperture sized and shaped to slidingly receive a guidewire.

In at least one exemplary embodiment of a method for preventing stroke of the present disclosure, the method comprises the steps of introducing a first stent having two or more convex struts into a body, navigating the first stent within the body until the first stent reaches an aortic arch, and positioning the first stent within a first vessel branching from the aortic arch so that the two or more convex struts are positioned either approximately perpendicular to, or in a direction of, blood flow within the aortic arch. In another embodiment, the step of introducing a first stent having two or more convex struts into a body comprises introducing a device for preventing stroke into a body, the device comprising an extension portion sized and shaped to fit within the vessel extending from the aortic arch, and a flange portion sized and shaped to prevent the device from advancing into the artery extending from the aortic arch in which the device may be positioned, the flange portion comprising the two or more parallel convex struts positioned across an opening defined within the flange portion, the struts capable of diverting an embolus from entering the artery when the device is positioned within the artery. In yet another embodiment, the step of positioning the first stent is performed by aligning the first stent within the vessel by detecting one or more radiopaque markers positioned upon the first stent. In an additional embodiment, the step of positioning the first stent comprises positioning the first stent within an innominate artery.

In at least one exemplary embodiment of a method for preventing stroke of the present disclosure, the method further comprises the steps of introducing a second stent having two or more convex struts into the body; navigating the second stent within the body until the second stent reaches the aortic arch, and positioning the second stent within a second vessel branching from the aortic arch so that the two or more convex struts of the second stent are positioned either approximately perpendicular to, or in a direction of, blood flow within the aortic arch. In another embodiment, the step of positioning the second stent comprises positioning the second stent within a common carotid artery. In yet another embodiment, the step of positioning the first stent comprises positioning the first stent within an innominate artery, wherein the first stent is capable of diverting an embolus from entering the innominate artery, and wherein the second stent is capable of diverting the embolus from entering the common carotid artery.

In at least one exemplary embodiment of a method for preventing stroke of the present disclosure, the method comprises the steps of introducing a wire into a body via a body puncture, the wire having a distal end, navigating the wire within the body until the distal end of the wire reaches a desired location within an aorta, mounting at least a portion of a system for preventing stroke over the guidewire, the system comprising a hypotube having a distal end and a proximal end, a folder coupled to the distal end of the hypotube, the folder sized and shaped to receive at least a portion of a stent, a sleeve positioned circumferentially around the hypotube proximal to the folder, the sleeve sized and shaped to receive at least a portion of the stent, and a stent, wherein a first part of the stent is positioned within the folder, and wherein a second part of the stent is positioned within the sleeve, advancing at least a portion of the system for preventing stroke within the body until the distal end of the hypotube is positioned within an artery branching from the aorta, and deploying the stent wherein at least a portion of the stent is positioned within the artery and wherein at least a portion of the stent is positioned within the aorta. In another embodiment, the step of deploying the stent comprises the step of pulling the sleeve away from the stent to deploy the first portion of the stent. In yet another embodiment, the step of deploying the stent further comprises the step of advancing the hypotube into the artery to deploy the second portion of the stent. In an additional embodiment, the step of deploying the stent further comprises the step advancing a conical dilator comprising a tapered distal end along the hypotube so that the tapered distal end of the conical dilator engages the folder. In an additional embodiment, the method further comprises the step of withdrawing the portion of the system within the body from the body.

BRIEF DESCRIPTION OF THE DRAWINGS

FIG. 3A shows exemplary devices for the prevention of stroke positioned within arteries extending from a portion of an aorta with the convex struts in alignment with blood flow, according to the present disclosure;

FIGS. 7A and 7B show additional embodiments of an exemplary system for preventing stroke, according to the present disclosure; and FIGS. 8A-8E show various steps of a method for positioning a device within a body, according to the present disclosure.

DETAILED DESCRIPTION

Figure 1:
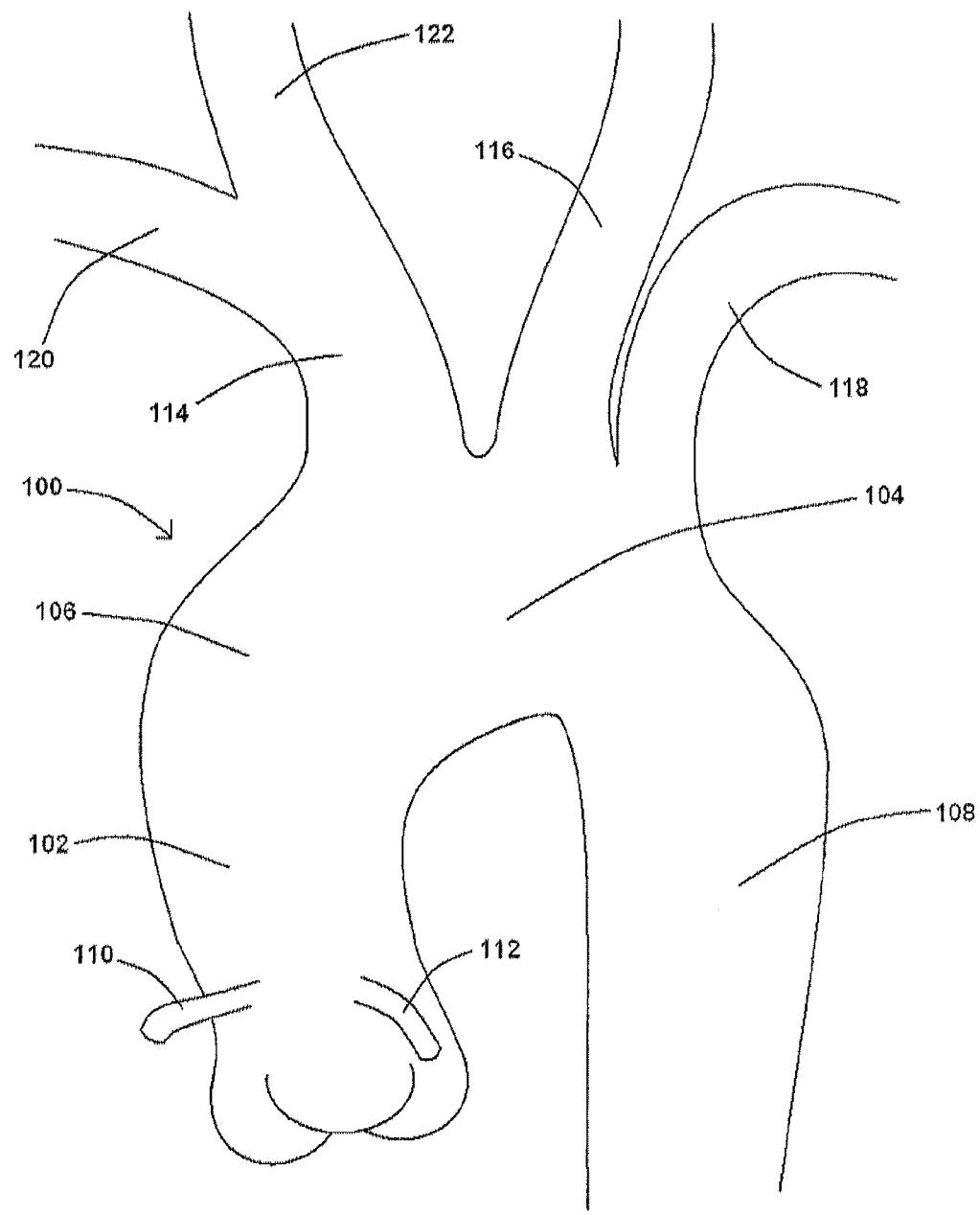
FIG. 1 shows a diagram of at least a portion of an aorta, according to the present disclosure.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The disclosure of the present application provides various devices, systems, and methods for the prevention of stroke. The devices, systems, and methods disclosed herein facilitate stroke prevention, in part, by addressing specific areas of the heart.

A diagram of at least a portion of an exemplary aorta is shown in FIG. 1. An aorta 100 is the main trunk of a vascular system which conveys oxygenated blood to the tissues of a body. It begins at the upper part of the left ventricle, where it may be approximately 3 cm in diameter in an adult human. As shown in FIG. 1, and at the union of the ascending aorta 102 with the aortic arch 104 (or the "arch of aorta"), the caliber of the vessel is increased, owing to a bulging of its right wall. This dilatation is termed the aortic bulb 106 (or bulb of the aorta), and on transverse section shows a somewhat oval figure. The ascending aorta 102 is contained within the pericardium, and is enclosed in a tube of the serous pericardium. It ascends for a short distance (the ascending aorta 102 is about 5 cm in length in an adult human), arches backward, and then descends within the thorax and abdomen (the descending aorta 108) and ends into the right and left common iliac arteries (about 1.7 cm in diameter in an adult human). The right coronary 110 and the left coronary 112, as shown in FIG. 1, branch from the ascending aorta 102.

There are three arteries that branch from the aortic arch 104, namely the innominate artery 114, the left common carotid artery 116, and the left subclavian artery 118. Instead of arising from the highest part of the aortic arch 104, these branches may spring from the commencement of the aortic arch 104 or the upper part of the ascending aorta 102. The distance between the aortic arch 104 or the upper part of the ascending aorta 102 at their origins may be increased or diminished, the most frequent variation being the approximation of the left common carotid artery 116 toward the innominate artery 114. In addition, and as shown in FIG. 1, the innominate artery 114 branches into the right subclavian artery 120 and the right common carotid artery 122.

Figure 2B:
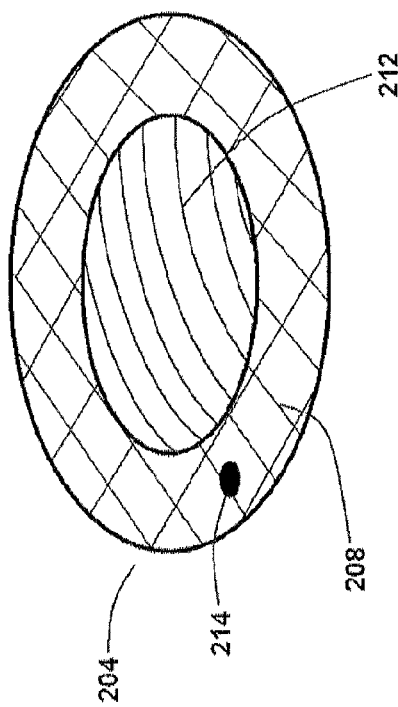
FIGS. 2A and 2B show exemplary embodiments of a device for the prevention of stroke, according to the present disclosure.
Figure 2C:
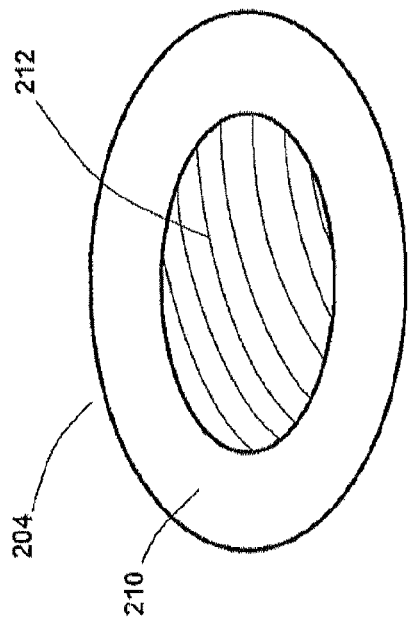
FIG. 2C shows an embodiment of a device comprising a planar flange, according to the present disclosure.
Figure 2A:
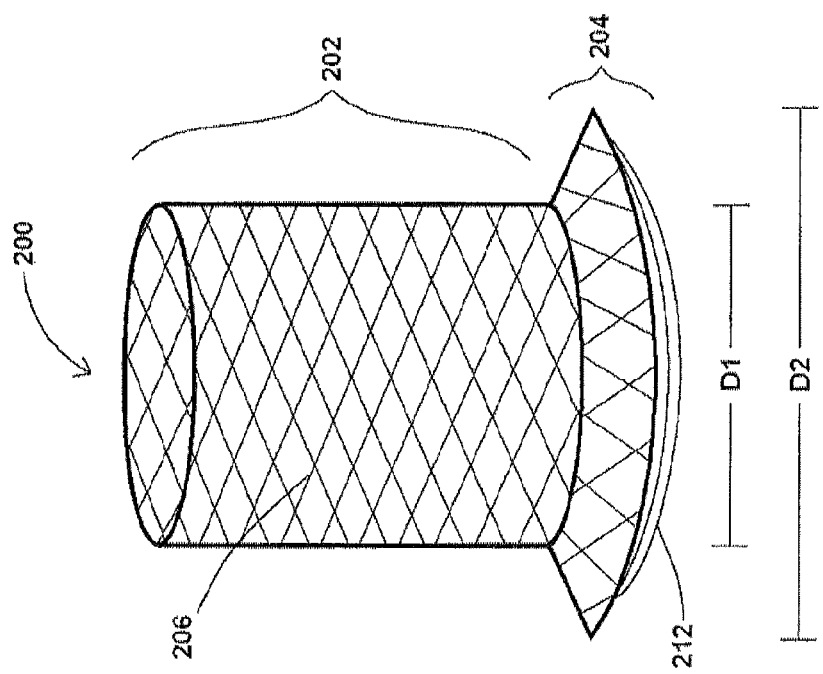

FIGS. 2A-2C show exemplary embodiments of a device of the present application for the prevention of stroke. As shown in FIG. 2A, an exemplary device 200 may comprise a stent comprising an extension portion 202 and a flange portion 204. Extension portion 202, as shown in FIG. 2A, may comprise a cylindrical stent sized and shaped to fit securely within an aortic branch. An exemplary extension portion 202 may comprise, for example, extension mesh 206 comprising multiple wires as shown in FIG. 2A. Flange portion 204 may comprise an inner diameter (shown as D1 in FIG. 2A) and an outer diameter (shown as D2), whereby D2 is larger than D1. In at least one embodiment, device 200 is collapsible, similar to a traditional stent.

In at least one embodiment of device 200 of the disclosure of the present application, device 200 comprises an autoexpandable metallic stent comprising a proximal flange (flange portion 204) and a distal cylindrical tube (extension portion 202). In an exemplary embodiment, extension portion 202 is approximately 1.5 cm to 2.5 cm in length. In at least one embodiment of device 200, the diameter of the stent is approximately 6 to 8 mm. Suitable material for a device 200 includes but is not limited to, stainless steel, cobalt-chromium-nickel-molybdenum-iron alloy, tantalum, nitinol, nickel-titanium, polymer materials, and various shape-memory polymers known in the art, including polyurethane, polytetrafluoroethylene or polytetrafluoroethene (PTFE), or another synthetic material.

Flange portion 204, as shown in the exemplary embodiments shown in FIGS. 2A and 2B, comprises flange mesh 208 comprising multiple wires. In another embodiment, and as shown in FIG. 2C, flange portion 204 comprises a planar flange 210 comprised of metal, plastic, or any other material suitable for such a flange portion 204.

As shown in FIGS. 2A-2C, flange portion 204 also comprises a plurality of convex struts 212 operable to divert, for example, an embolus, from entering the inner portion of device 200 (the inner portion defined by extension portion 202). Convex struts 212 are one example of such an embolus diversion portion of device 200, noting that other embodiments of an embolus diversion not comprising convex struts 212 may be useful with device 200. For example, and instead of convex struts 212, an exemplary embolus diversion portion may comprise a mesh (similar to, for example, extension mesh 206 and/or flange mesh 208), whereby such a mesh is operable to divert an embolus from entering the inner portion of device 200.

Convex struts 212, in an exemplary embodiment, are positioned along device 200 to cover the proximal orifice of the cylindrical stent (device 200). In at least one embodiment of a device 200 of the disclosure of the present application, the diameter of each convex strut 212 is approximately 0.25 mm to 0.5 mm, and the distance between each convex strut 212 is approximately 0.5 mm to 1.5 mm. Convex struts 212 may comprise material the same and/or similar to the material used to prepare other portions of device 200, and may also be a combination of a metal plus polyurethane, polytetrafluoroethylene or polytetrafluoroethene (PTFE), or another synthetic material.

In at least one embodiment, convex struts 212 may be semirigid or flexible in order to allow the removal of hypotube 402 (see FIG. 4) and/or allow the passage of a catheter stent device, including device 200, for stenting the carotid artery, for example, if it develops an atherosclerotid plaque. In an exemplary embodiment, the strut shape can be convex or semiconvex in order to be easily and constantly "washed" by the aortic blood flow and therefore avoid local thrombosis. If an emboli lands on a strut, the strut shape will also allow it to wash off to the periphery.

In addition, and in the exemplary embodiment shown in FIG. 2B, device 200 may further comprise one or more radiopaque markers 214 are located proximally and/or distally on device 200 to aid the placement of device 200 within a body.

Figure 3B:
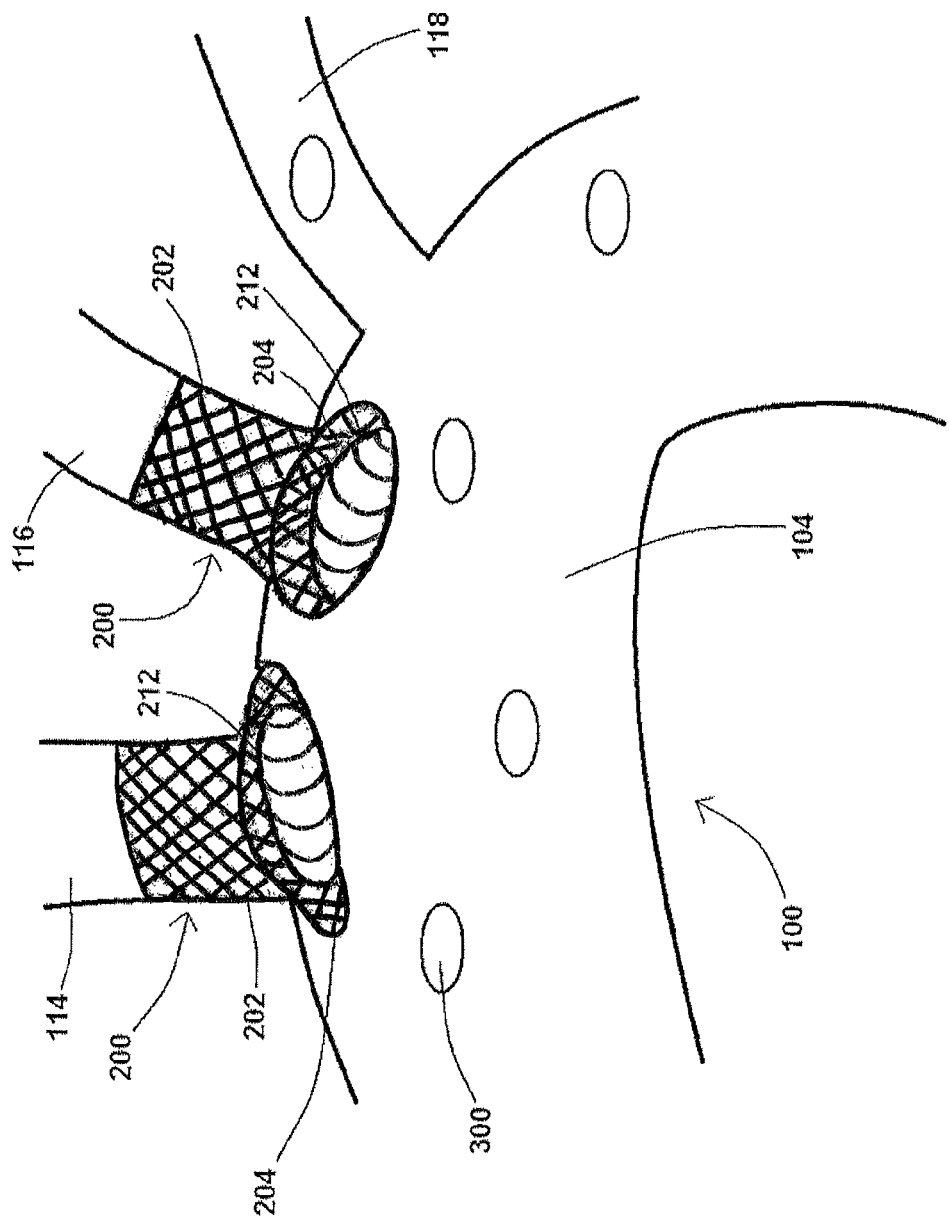
FIG. 3B shows exemplary devices for the prevention of stroke positioned within arteries extending from a portion of an aorta with the convex struts in alignment approximately perpendicular to blood flow, according to the present disclosure.

Exemplary devices for the prevention of stroke positioned within a portion of an aorta are shown in FIGS. 3A and 3B. As shown in FIGS. 3A and 3B, two devices 200 are shown positioned within arteries branching from aorta 100, with one device 200 positioned partially within innominate artery 114 and another device 200 positioned partially within left common carotid artery 116. Device 200 positioned within innominate artery 114 is positioned so that extension portion 202 is positioned within a portion of innominate artery 114 extending from aortic arch 104, and whereby flange portion 204 prevents device 200 from advancing further into innominate artery 114. Similarly, a device 200 is shown in FIGS. 3A and 3B positioned within left common carotid artery 116, so that extension portion 202 is positioned within a portion of left common carotid artery 116 extending from aortic arch 104, and whereby flange portion 204 prevents device 200 from advancing further into left common carotid artery 116. In at least one embodiment, flange portion 204 completely covers and exceeds the entrance of the artery in which device 200 is positioned. In an exemplary embodiment of device 200 positioned within an artery as referenced herein, the distal cylindrical portion of the stent (extension portion 202 of device 200) anchors device 200 by way of radial force within the artery for which device 200 is placed.

As shown in the exemplary embodiments of device 200 shown in FIG. 3A, convex struts 212 are aligned in a direction similar to the flow of blood within aorta 100. In such an alignment, and as blood flows through aorta 100, an embolus 300 which may be present within aorta 100 (specifically within the aortic arch 104) would be guided along convex struts 212. As shown in FIG. 3B, devices 200 are aligned in a direction approximately perpendicular to the flow of blood within aorta 100. In such an alignment, an embolus 300 present within aorta 100 would potentially contact convex struts 212 and be deflected therefrom with little or no risk of embolus 300 being trapped therein.

As shown in FIGS. 3A and 3B, an embolus 300 is prevented from entering the innominate artery 114 and the left common carotid artery 116, but is permitted to enter the left subclavian artery 118. As such, and in this example, an embolus 300 present within the aorta is effectively prohibited from being advanced to the brain, as an embolus 300 cannot enter the innominate artery 114 and the left common carotid artery 116 because devices 200 are positioned within each of those arterial openings. Such an arrangement of devices 200 may then effectively prevent a patient from having a stroke based upon the introduction of an embolus 300 from the aortic arch 104 to the brain.

In summary, and as described above with respect to FIGS. 3A and 3B, for example, the disclosure of the present application provides a device 200, which may be referred to as a percutaneous carotid emboli rerouting device, to be delivered individually to arteries given off by the aortic arch (namely the innominate artery 114, the left common carotid artery 116, and the left subclavian artery 118) in order to avoid the passage of the embolic or thromboembolic material (an embolus 300, which may be, for example, a clot, calcium, etc.) to the vascular brain system. Such an arrangement of devices 200 would then prevent thromboembolic stroke in patients with different cardiovascular diseases from cardiac origin.

At least one goal of the devices, systems, and methods of the present disclosure is to reroute an embolus distally to the arterial system (iliac or femoral arteries) to avoid disabling stroke, decrease mortality and avoid physical impairment with a poor quality of life. Unlike stroke, medical or surgical treatment of the peripheral arterial embolus (fibrinolitic drugs, surgical embolectomy, or endovascular embolus suction) can be provided with little residual effects.

Figure 4:
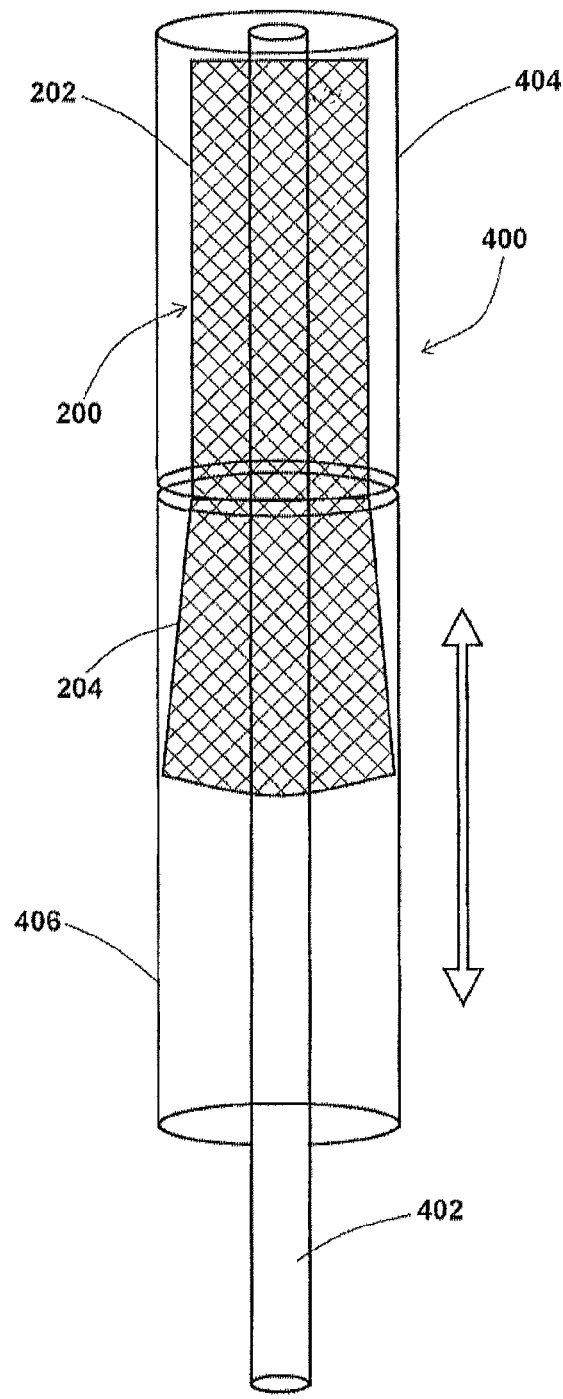
FIG. 4 shows an exemplary embodiment of a system for preventing stroke, according to the present disclosure.

An exemplary embodiment of a system for preventing stroke of the present disclosure is shown in FIG. 4. As shown in FIG. 4, system 400 comprises a hypotube 402 having a distal end and a proximal end, and in at least one exemplary embodiment, hypotube 402 comprises a folder 404 coupled to the distal end of hypotube 402. In the embodiment shown in FIG. 4, system 400 further comprises a device 200, whereby an extension portion 202 of device 200 is shown positioned within at least part of folder 404, and whereby a flange portion 204 of device 200 is positioned within at least part of a sleeve 406 positioned around hypotube 402 proximal to folder 404. Sleeve 406, as shown in this exemplary embodiment, slidingly engages hypotube 402 and may be moved in a forward or backward direction as indicated by the arrow in the figure.

In at least one embodiment, device 200 is an autoexpandable metallic stent mounted over a hypotube 402 as shown in FIG. 4. Device 200 may be compressed by sleeve 406 and folder 404. In at least one embodiment, at least part of system 400 has a diameter of 7 Fr to 8 Fr (2.3 to 2.7 mm), with an exemplary device 200 having a compressed diameter of about 1.8 to 2.0 mm.

Figure 5A:
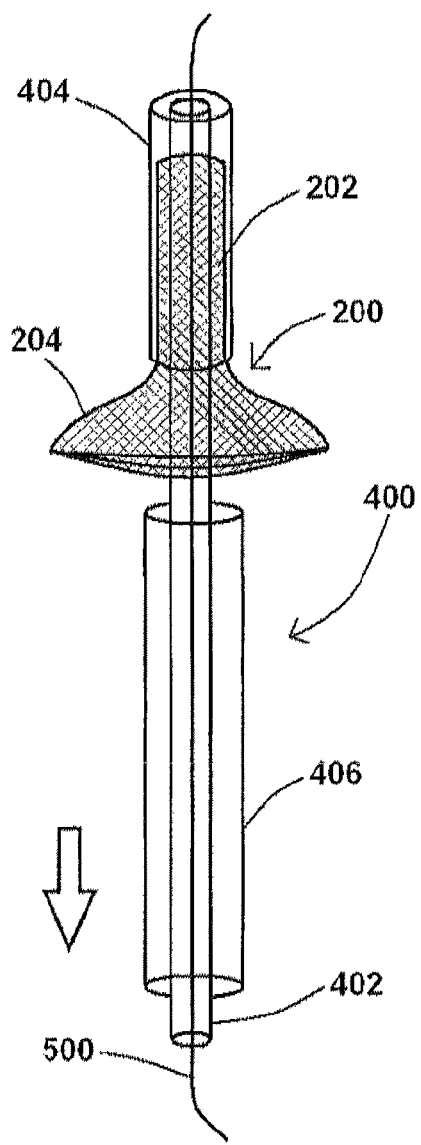
FIGS. 5A and 5B show an exemplary system of the present disclosure with portions thereof being moved to allow for device deployment, according to the present disclosure.
Figure 5B:
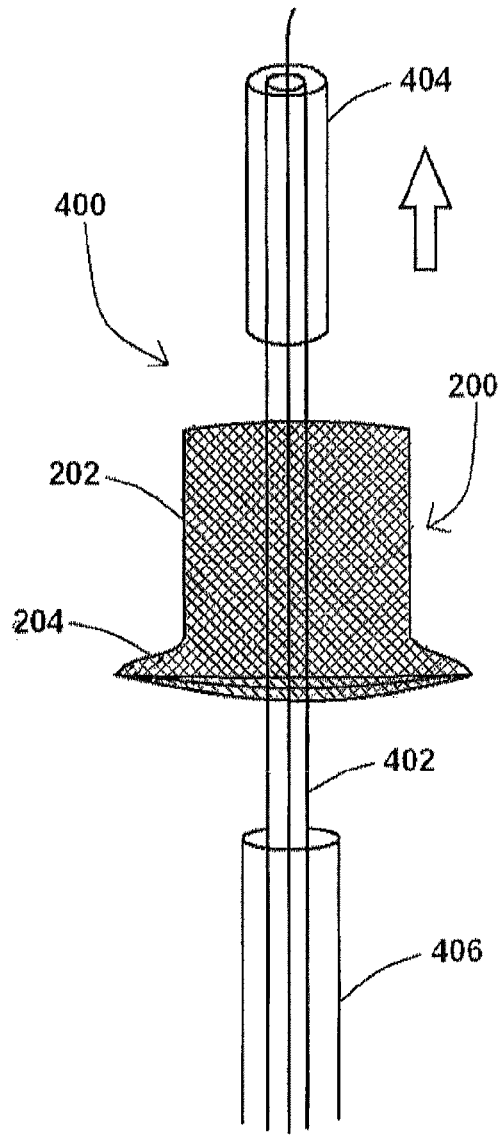

FIGS. 5A and 5B show exemplary embodiments of at least portions of systems for preventing stroke of the present disclosure. As shown in FIG. 5A, an exemplary system 400 comprises hypotube 402 to which folder 404 is coupled thereto. System 400, as shown in FIGS. 5A and 5B, further comprises sleeve 406 slidingly engaged around hypotube 402. Device 200 may be positioned at least partially within folder 404 and sleeve 406 prior to deployment, whereby the extension portion 202 of device 200 may be positioned within at least part of folder 404, and whereby the flange portion 204 of device 200 may be positioned within at least part of a sleeve 406 (as shown in FIG. 4).

As shown in FIG. 5A, device 200 may be partially deployed as follows. First, and in an exemplary method of positioning a stent within a body, a wire 500 (a guide wire, for example) may be advanced within a body at or near a desired location of device 200 deployment. When wire 500 has been advanced, hypotube 402, along with any portions of system 400 coupled to hypotube, may be advanced along wire 500 within the body. As shown in FIG. 4, initial advancement of at least a portion of system 400 may comprise advancement of hypotube 402, folder 404, sleeve 406, and device 200 positioned within folder 404 and sleeve 406.

When device 200 has been positioned within a body at or near a desired position, sleeve 406 may be withdrawn toward the proximal end of hypotube 402 (in the direction of the arrow shown in the figure). This step may be performed prior to, during, or after the step of positioning the distal end of hypotube 402 within a vessel (for example, a vessel branching off the aortic arch 104). As sleeve 406 is slid toward the proximal end of hypotube 402, the flange portion 204 of device 200 is allowed to expand as shown in FIG. 5A.

Further deployment of device 200 within a body is shown in FIG. 5B. As shown in FIG. 5B, and upon movement of folder 404 away from device 200 (in a direction shown by the arrow in the figure, for example), extension portion 202 of device 200 may deploy as shown in FIG. 5B. As folder 404 is moved away from device 200 (by, for example, advancement of hypotube 402 within a body), extension portion 202 of device 200 is no longer positioned within folder 404, thereby permitting expansion/deployment of extension portion 202.

Figures 6A, 6B:
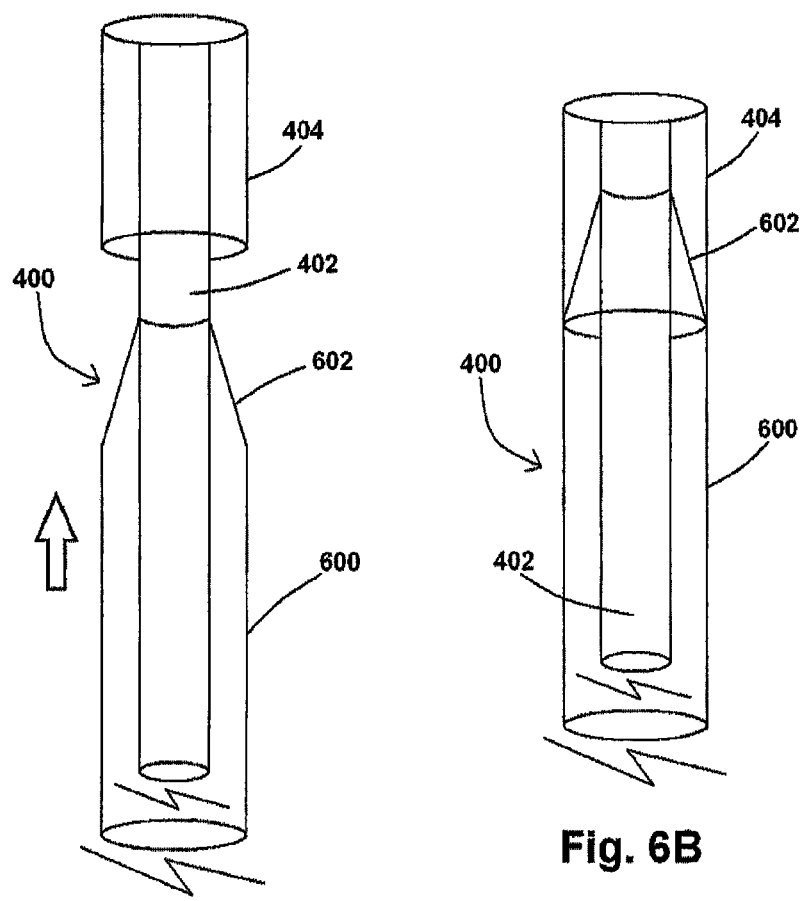
FIGS. 6A and 6B show at least a portion of an exemplary system for preventing stroke, said system comprising a conical dilator useful to facilitate removal of at least a portion of the exemplary system from the body, according to the present disclosure.

FIGS. 6A and 6B show exemplary embodiments of at least a portion of a system for preventing stroke. In at least one embodiment, system 400 comprises a conical dilator 600 slidingly engaged around a hypotube 402 coupled to a folder 404. As shown in FIG. 6A, an exemplary conical dilator 600 may comprise a tapered distal end 602, wherein the tapered distal end 602 is sized and shaped to engage the inside of folder 404. To engage folder 404, conical dilator 600 may slide along hypotube 402 in a direction indicated by the arrow in FIG. 6A. An exemplary embodiment of the engagement of conical dilator 600 and folder 404 is shown in FIG. 6B.

Engagement of conical dilator 600 with folder 404, as shown in FIGS. 6A and 6B, may facilitate the removal of at least a portion of system 400 from a body after positioning device 200. For example, and as shown in FIGS. 5A and 5B, after deployment of device 200 within a body, the portion of system 400 comprising folder 404 is positioned, for example, further within a vessel than device 200. Removal of the portion of the system 400 comprising hypotube 402 and folder 404 would require, for example, pulling that portion of system 400 back through device 200. As shown in the exemplary embodiments of FIGS. 5A-6B, folder 404 may, for example, become caught on device 200 and/or a portion of a body, preventing effective removal of that portion of system 400.

In at least one embodiment, and by engaging folder 404 with conical dilator 600, folder 404, along with the portion of system 400 coupled to folder 404, may be removed from a body after placement of a device 200 as shown in FIGS. 7A and 7B. As shown in FIG. 7A, and after a device 200 has been deployed, a user of system 400 may slide a conical dilator 600 along hypotube 402 in a direction indicated by the arrow. Conical dilator 600, in the example shown in FIGS. 7A and 7B, would be sized and shaped as to fit within the spaces between convex struts 212 of device 200. After conical dilator 600 has engaged folder 404, as shown in FIG. 7B, hypotube 402 may be withdrawn from the body in a direction indicated by the arrow, and because of the engagement, folder 404 may be removed from the body without becoming caught on device 200.

In at least one embodiment of a system for preventing stroke of the present disclosure, system 400 comprises a device 200, a hypotube 402, and a folder 404 coupled to hypotube 402 at or near the distal end of hypotube 402. Device 200, in at least one embodiment, may be autoexpandable, i.e. device 200 has a "memory" allowing it to expand to a native configuration after being retracted/compressed to fit within, for example, folder 404 and sleeve 406. System 400, in at least one embodiment, may further comprise, or be used in connection with, a femoral catheterization kit known and used in the marketplace.

In at least one exemplary method of positioning device 200 within a body of the present disclosure, the percutaneous placement of the percutaneous carotid emboli rerouting device (device 200) may be performed in an angiography procedure room. Prior to positioning device 200, a user may perform a contrast aortogram, for example, to map out the aortic arch 104 and where the cerebral vessels merge with aortic arch 104. For safety, patient preparation and sterile precautions are recommended as for any angioplasty procedure.

In at least one embodiment of a method for preventing stroke, the method comprises the step of performing a percutaneous angiogram using technique(s) known in the art under local anesthesia. As referenced above, the percutaneous angiogram would map the aortic arch 104 so that a user of a device 200 and/or system 400 of the disclosure of the present application would, for example, be able to select an appropriately-sized device 200 and/or system 400 (or portion(s) thereof) when performing the procedure. A user may also introduce a wire 500 (such as guide wire as shown in FIG. 5A) to reach the innominate artery 114 and/or the left common carotid artery 116. After wire 500 has been positioned, portions of system 400 may be mounted over the guide wire and progressed to the level of the entrance of the innominate artery 114 and/or the left common carotid artery 116. Said portions of system 400 may include hypotube 402 and a folder 404 distally mounted thereto, and may further comprise a sleeve 406, wherein an exemplary device 200 may be positioned at least partially within folder 404 and sleeve 406, as shown in FIG. 8A.

Deployment of device 200, in an exemplary embodiment of a method of the present application for performing the same, is as a follows. Under fluoroscopy, sleeve 406 may be pulled back to allow the delivery of the proximal portion of the stent (the flange portion 204 of device 200) as shown in FIG. 8B. The diameter of flange portion 204 that exceeds the diameter of the innominate artery 114 and/or the left common carotid artery 116 impedes the progression of device 200 within said arteries, thus giving the user/operator time to deliver and anchor the second portion of the stent (the extension portion 202 of device 200), by, for example, forward progression of hypotube 402 as shown in FIGS. 5B and 8C. When device 200 has been positioned, removal of hypotube 402 and folder 404 may be removed from the body, for example, by introducing conical dilator 600 as described herein. In at least one example, the tapered distal end 602 of conical dilator 600 is advanced until it engages folder 404 of hypotube 402, as shown in FIGS. 6A-7B, 8D and 8E, effectively forming a single unit (conical dilator 600+hypotube 402+optionally wire 500 (not shown)). This "unit" may then removed through the convex struts 212 as shown in FIG. 8E, and distally to the femoral artery for which at least part of system 400 was initially introduced.

The various devices, systems, and methods for preventing stroke of the present disclosure have various benefits to patients with various diseases and/or disorders of the heart and/or circulatory system. For example, patients with chronic atrial fibrillation (non-valvular atrial fibrillation), recurrence transient ischemic attack, atrial fibrillation and anticoagulation contraindications, and/or left atrial appendage thrombosis may have their risk of stroke either reduced or eliminated by way of an exemplary devices, systems, and/or method of the present disclosure. In addition, patients with acute myocardial infarct with left ventricular thrombus, atrial flutter (ablation and pulmonary vein isolation), cardiomyopathy with left ventricular enlargement, non-obstructive thrombus of a mechanical heart valve, patent foramen ovale (cryptogenic ischemic stroke) and/or an acute infection endocardiatis with valve vegetation without valve insufficiency under medical treatment (vegetation>1 cm which currently oblige to surgical remotion) may also benefit from the present disclosure.

While various embodiments of devices, systems, and methods for the prevention of stroke have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

We claim:

1. A device for the prevention of stroke, the device comprising:
 an extension portion sized and shaped to fit within an artery extending from an aortic arch and comprising a proximal end and a distal end; and
 an expandable, non-bulbous, annular flange portion coupled with the proximal end of the extension portion, the flange portion comprising an inner diameter and sized and shaped to prevent the device from advancing into an artery extending from the aortic arch in which the device may be positioned, the flange portion consisting essentially of a perimeter, an opening, and two or more parallel convex struts and no other struts, the two or more parallel convex struts each comprising an exterior surface and extending from the flange portion across the opening, and wherein the two or more parallel convex struts are spaced apart from each other to define unbroken parallel apertures that span the opening, configured to protrude into a path of blood flow within a vasculature adjacent to the artery, and capable of diverting an embolus within the path of blood flow within the vasculature from entering the artery when the device is positioned within the artery;

wherein the flange portion does not define any apertures within the opening other than the parallel apertures, and the perimeter surrounds the two or more convex struts and, when expanded, further comprises an outer diameter that is larger than the inner diameter; and wherein no part of the exterior surfaces of the two or more parallel convex struts comprises a concave shape.

2. The device of claim 1, wherein the two or more parallel convex struts comprises four or more parallel convex struts.

3. The device of claim 2, wherein the two or more parallel convex struts are positioned between about 0.5 mm to 1.5 mm from one another.

4. The device of claim 1, wherein when the device is positioned within the artery extending from an aortic arch, the two or more parallel convex struts are positioned approximately perpendicular to a direction of blood flow within the aortic arch.

5. The device of claim 1, wherein when the device is positioned within the artery extending from an aortic arch, the two or more parallel convex struts are positioned in a direction of blood flow within the aortic arch.

6. The device of claim 1, wherein the device comprises a stent.

7. The device of claim 6, wherein the stent is autoexpandable.

8. The device of claim 1, wherein the extension portion comprises a substantially cylindrical shape.

9. The device of claim 1, wherein the extension portion comprises an autoexpandable stent comprising multiple wires.

10. The device of claim 1, wherein the extension portion has a length between about 1.5 cm to about 2.5 cm.

11. The device of claim 1, wherein the extension portion has a diameter between about 6 mm to about 8 mm when the extension portion is in an expanded configuration.

12. The device of claim 1, wherein the extension portion has a diameter between about 1.8 mm to about 2.0 mm when the extension portion is in a compressed configuration.

13. The device of claim 1, wherein the device is comprised of a material selected from the group consisting of stainless steel, cobalt-chromium-nickel-molybdenum-iron alloy, tantalum, nitinol, nickel-titanium, polymer materials, and a shape-memory polymer.

14. The device of claim 1, wherein the flange portion further comprises a flange mesh comprising multiple wires, wherein the flange mesh is configured so that, when expanded, the outer diameter of the perimeter of the flange portion exceeds an entrance diameter of, but does not extend across a lumen of, the artery when the device is positioned within the artery.

15. The device of claim 1, wherein the flange portion comprises a planar flange.

16. The device of claim 1, further comprising:
one or more radiopaque markers positioned upon the flange portion relative to the two or more parallel convex struts.

17. The device of claim 16, wherein when the device positioned within the artery extending from an aortic arch, the one or more radiopaque markers facilitate alignment of the device so that the two or more parallel convex struts are positioned approximately perpendicular to a direction of blood flow within the aortic arch.

18. The device of claim 16, wherein when the device positioned within the artery extending from an aortic arch, the one or more radiopaque markers facilitate alignment of the device so that the two or more parallel convex struts are positioned in a direction of blood flow within the aortic arch.

19. The device of claim 1, wherein the diameter of each of the two or more parallel convex struts is between about 0.25 mm and 0.5 mm.

20. The device of claim 1, wherein the two or more parallel convex struts are flexible.

21. The device of claim 1, wherein the opening defined within the flange portion corresponds to a lumen of the artery in which the device may be positioned, and whereby no other struts are positioned across the opening defined within the flange portion in addition to the two or more parallel convex struts positioned across the opening defined within the flange portion.

22. A device for the prevention of stroke, the device consisting of:
an extension portion sized and shaped to fit within an artery extending from an aortic arch and comprising a proximal end and a distal end; and
a non-bulbous flange portion coupled with the proximal end of the extension portion, the flange portion consisting of an expandable, annular positioning portion comprising an inner diameter and sized and shaped to prevent the device from advancing into an artery extending from the aortic arch in which the device may be positioned, and a convex diverting portion extending from the annular positioning portion that is configured to divert an embolus from entering the artery extending from the aortic arch when the device is positioned within the artery;
wherein the diversion of the embolus is caused by the embolus deflecting off of the diverting portion consisting essentially of two or more parallel convex struts and no other struts spanning across an opening defined within the diverting portion that corresponds to a lumen of the artery, the two or more parallel convex struts spaced apart from each other to define unbroken parallel apertures that span the opening; and
wherein the positioning portion further comprises a continuous perimeter that surrounds the two or more parallel convex struts, is concentric with the opening and, when expanded, the perimeter comprises an outer diameter that is larger than the inner diameter.

23. A device for the prevention of stroke, the device comprising:
an extension portion comprising a substantially cylindrical shape, the extension portion sized and shaped to fit within an artery extending from an aortic arch and comprising a proximal end and a distal end;
an expandable, non-bulbous, annular flange portion coupled with the proximal end of the extension portion, the annular flange portion comprising an inner diameter and sized and shaped to prevent the device from advancing into an artery extending from the aortic arch in which the device may be positioned, the flange portion consisting essentially of a continuous perimeter, an opening, and two or more parallel convex struts each comprising an exterior surface and extending from the annular flange portion across the opening, and wherein the two or more parallel convex struts are spaced apart from each other to define unbroken parallel apertures that span the opening, configured to protrude into a path of blood flow within a vasculature adjacent to the artery, and capable of diverting an embolus within the path of blood flow within the vasculature from entering the artery when the device is positioned within the artery; and one or more radiopaque markers positioned upon the flange portion, wherein when the device is positioned within the artery extending from an aortic arch, the one or more radiopaque markers facilitate alignment of the device, the alignment selected from the group consisting of an alignment so that the two or more parallel convex struts are positioned approximately perpendicular to a direction of blood flow within the aortic arch and an alignment so that the two or more parallel convex struts are positioned in a direction of blood flow within the aortic arch;

wherein the flange portion does not define any apertures within the opening other than the parallel apertures, and the perimeter surrounds the two or more parallel convex struts and, when expanded, further comprises an outer diameter that is larger than the inner diameter; and wherein no part of the exterior surfaces of the two or more parallel convex struts comprises a concave shape.

24. The device of claim 23, wherein the diameter of each of the two or more parallel convex struts is between about 0.25 mm and 0.5 mm, and wherein the two or more parallel convex struts are positioned between about 0.5 mm to 1.5 mm from one another.

25. A device for the prevention of stroke, the device consisting of:

an extension portion comprising a substantially cylindrical shape, the extension portion sized and shaped to fit within an artery extending from an aortic arch and comprising a proximal end and a distal end; and a non-bulbous flange portion coupled with the proximal end of the extension portion, the flange portion comprising an expandable, annular positioning portion sized and shaped to prevent the device from advancing into an artery extending from the aortic arch in which the device may be positioned, the annular positioning portion comprising an inner diameter and a convex diverting portion consisting essentially of an opening and two or more parallel convex struts and no other struts, the two or more parallel convex struts each comprising an exterior surface and extending from the annular positioning portion across the opening, and wherein the two or more parallel convex struts are spaced apart from each other to define unbroken parallel apertures that span the opening, configured to protrude into a path of blood flow within a vasculature adjacent to the artery, and capable of diverting an embolus within the path of blood flow within the vasculature from entering the artery when the device is positioned within the artery;

wherein the diverting portion does not define any apertures within the opening other than the parallel apertures and the perimeter of the positioning portion surrounds the two or more parallel convex struts and, when expanded, further comprises an outer diameter that is larger than the inner diameter; and wherein no part of the exterior surfaces of the two or more parallel convex struts comprises a concave shape.

26. The device of claim 25, wherein the diameter of each of the two or more parallel convex struts is between about 0.25 mm and 0.5 mm, and wherein the two or more parallel convex struts are positioned between about 0.5 mm to 1.5 mm from one another.

\* \* \* \* \*